(12) United States Patent
Hovorka et al.

(10) Patent No.: US 9,655,739 B2
(45) Date of Patent: May 23, 2017

(54) INTERVERTEBRAL DISC PROSTHESIS (71) Applicant: LDR Medical

(72) Inventors: Istvan Hovorka, Nice (FR); Pierre Bernard, Bordeaux (FR)

(73) Assignee: LDR Medical, Sainte-Savine (FR)

( * ) Notice: Subject to any disclaimer, the term of this patent is extended or adjusted under 35 U.S.C. 154(b) by 130 days.

(21) Appl. No.: 14/513,818

(22) Filed: Oct. 14, 2014

(65) Prior Publication Data
US 2015/0032209 A1 Jan. 29, 2015

Related U.S. Application Data

(63) Continuation of application No. 11/051,710, filed on Feb. 4, 2005, now Pat. No. 8,858,635.

(30) Foreign Application Priority Data

Feb. 4, 2004 (FR) ...................................... 04 01024

(51) Int. Cl.
| | |
|---|---|
| *A61F 2/44* | (2006.01) |
| *A61F 2/46* | (2006.01) |
| *A61B 17/34* | (2006.01) |
| *A61F 2/00* | (2006.01) |
| *A61F 2/30* | (2006.01) |

(52) U.S. Cl.
CPC .......... *A61F 2/4425* (2013.01); *A61F 2/4611* (2013.01); *A61B 17/3468* (2013.01); *A61B 17/3472* (2013.01); *A61F 2/0095* (2013.01); *A61F 2/30767* (2013.01); *A61F 2002/30331* (2013.01); *A61F 2002/30365* (2013.01); *A61F 2002/30367* (2013.01); *A61F 2002/30369* (2013.01); *A61F 2002/30387* (2013.01); *A61F 2002/30476* (2013.01); *A61F 2002/30571* (2013.01); *A61F 2002/30616* (2013.01); *A61F 2002/30649* (2013.01); *A61F 2002/30662* (2013.01); *A61F 2002/30673* (2013.01); *A61F 2002/30685* (2013.01); *A61F 2002/30795* (2013.01); *A61F 2002/30841* (2013.01); *A61F 2002/30904* (2013.01); *A61F 2002/30937* (2013.01); *A61F 2002/443* (2013.01); *A61F 2002/4622* (2013.01); *A61F 2220/0025* (2013.01); *A61F 2220/0033* (2013.01)

(58) Field of Classification Search
CPC .............. A61F 2/4425; A61F 2002/443; A61F 2002/30662
See application file for complete search history.

*Primary Examiner* — Christopher D Prone
(74) *Attorney, Agent, or Firm* — Lauff Law PLLC (57) ABSTRACT

This disclosure relates to intervertebral disc prostheses which may have an upper plate, a lower plate, and a mobile core, with the upper surface of the core being in contact with at least a part of the lower surface of the upper plate. In some configurations, limit stops reduce friction while limiting or preventing the movements of the core relative to the lower plate, in translation and in rotation, respectively, along an axis substantially parallel to the lower plate and about an axis substantially perpendicular to the lower plate. Instrumentation for insertion of the prostheses into intervertebral spaces is also described.

20 Claims, 7 Drawing Sheets

INTERVERTEBRAL DISC PROSTHESIS

RELATED APPLICATIONS

This application is a continuation of U.S. patent application Ser. No. 11/051,710 filed Feb. 4, 2005, and issuing as U.S. Pat. No. 8,858,635 on Oct. 14, 2014, which claims priority under 35 U.S.C. §119 to French Patent Application No. 0401024 filed in FRANCE on Feb. 4, 2004.

TECHNICAL FIELD

The present invention relates to intervertebral disc prostheses.

BACKGROUND

Various types of prostheses are known in the prior art. Numerous prostheses are constituted by a lower plate and an upper plate enclosing a central core. A part of these prostheses enables the upper plate to slide relative to the central core and optionally permits the central core to slide relative to the lower plate. This sliding of the central core relative to the lower plate allows spontaneous positioning of the core in the ideal position to absorb constraints imposed on the prosthesis during movements made by the patient carrying the prosthesis. However, because of the forces from applied constraints, materials utilized and the form of the different pieces constituting the prosthesis, the sliding of the core is often difficult, which causes rapid wear and heightens the risk of ejection of at least a part of the prosthesis to the outside of the spine, and this is not desirable for the patient.

An intervertebral disc prosthesis is provided that allows movement of the different pieces of the prosthesis between one another, but facilitates core sliding.

Intervertebral disc prostheses in accordance with the present invention comprise at least three pieces including a first plate, a second plate and a core that is mobile relative to at least one of the plates. In a preferred embodiment, the core has a curved surface in contact with at least a part of a complementary curved surface of the first plate and a substantially flat surface in contact with at least a part of a substantially flat surface of the second plate, and limit stops situated near the periphery of the second plate and of the core that limit or prevent, without excessive friction, the movements in translation of the core relative to the second plate, along an axis substantially parallel to the substantially flat surfaces, and limit or prevent the movements in rotation of the core relative to the second plate, about an axis substantially perpendicular to the substantially flat surfaces. In a preferred embodiment, the substantially flat surface of the core has at least one dummy hole facilitating sliding of the core relative to the substantially flat surface of the second plate with which it is in contact.

According to another particular feature in an embodiment, the lower surface of the core and the upper surface of the second plate, known as the lower plate, are substantially flat.

According to another particular feature in an embodiment, at least the substantially flat surface of the core is enclosed in a protective shell, whereof the surface in contact with the substantially flat surface of the second plate and with the substantially flat of the core has at least one hole.

According to another particular feature in an embodiment, the protective shell of the core does not cover the limit stops of the core, so as to avoid contact of the protective shell with the limit stop of the second plate.

According to another particular feature in an embodiment, the area of contact of the substantially flat surface of the core or of the protective shell with the substantially flat surface of the second plate and the area of contact of the curved surface of the core with the curved surfaces of the first plate are substantially equal, on both sides of the core.

According to another particular feature in an embodiment, the angle formed by the edges of the hole present at least on the substantially flat surface of the core or of the protective shell of the core is softened to improve the sliding of the core or of the shell on the substantially flat surface of the second plate.

According to another particular feature in an embodiment, the hole present on the substantially flat surface of the core or of the protective shell of the core is prolonged, as far as the periphery of this substantially flat surface, by grooves forming channels via which the interstitial liquid from surrounding tissue can play a lubricating role to improve the sliding of the core on the substantially flat surface of the second plate, when the prosthesis is in place on the patient.

According to another particular feature in an embodiment, the angle formed by the edges of the grooves prolonging the hole as far as the periphery of the substantially flat surface of the core or of the protective shell of the core is softened to improve the sliding of the core or of the shell on the substantially flat surface of the second plate.

According to another particular feature in an embodiment, the core is made of polyethylene.

According to another particular feature in an embodiment, the protective shell of the core is made of metal.

According to another particular feature in an embodiment, the first and second plates are made of metal.

According to another particular feature in an embodiment, the limit stops consist of male structure of the second plate, cooperating with female structure of the core.

According to another particular feature in an embodiment, the core is mobile relative to the first and/or second plates and that a variable angle between the first and second plates depends on the position of the core, an inclination, in any direction at all, of at least the first plate inducing the displacement of the core between the plates and providing freedom of movement for the patient and, at the same time, helping eliminate the positioning defects of the prosthesis.

According to another particular feature in an embodiment, an angle between the upper surface of the upper plate and the lower surface of the lower plate can be imposed either by the fact that the plane means representing the upper and lower surfaces of the core form an angle, or by the fact that the plane means representing the upper and lower surfaces of the first plate and/or of the second plate form an angle, or by restriction of the movements of the core about a position imposing inclination of at least the first plate.

According to another particular feature in an embodiment, the same plates can be assembled with cores of different thicknesses.

According to another particular feature in the embodiment, at least a part of the surface of the first plate is concave and complementary to the surface of the core with which it is in contact.

According to another particular feature in the embodiment, the dimensions of each male structure are slightly less than those of each female structure so as to permit slight clearance between the core and the second plate.

According to another particular feature in the embodiment, the dimensions of each male structure are substantially the same as those of each female structure so as to prevent any clearance between the core and the second plate.

According to another particular feature in the embodiment, the male structure of the second plate are two contact plates situated opposite one another on two edges of the prosthesis, and the female structure of the core are two recesses.

According to another particular feature in the embodiment, the male structure of the second plate are two walls situated opposite one another in the vicinity of two edges of the prosthesis, and in that the female structure of the core are recesses.

According to another particular feature in the embodiment, the male structure of the lower plate are two nibs curved towards the interior of the prosthesis and situated opposite one another on two edges of the prosthesis, and the female structure of the core are two recesses.

According to another particular feature in the embodiment, at least one of the nibs is replaced by a pin equipped with a hole and on which a plate is fixed by means of a dowel penetrating the hole.

According to another particular feature in the embodiment, the lower surface of the lower plate and the upper surface of the upper plate are provided with teeth or notches situated in the vicinity of at least two edges of the prosthesis and oriented so as to prevent sliding of the prosthesis prior to its adhesion to the osseous tissue permitted by a porous biocompatible coating of the surfaces of the plates in contact with the vertebrae.

According to another particular feature in the embodiment, at least the second plate comprises one or more openings in the vicinity of its front side, provided to receive anchoring means of the prosthesis in a vertebra.

According to another particular feature in the embodiment, the openings of the second plate are circular, and in that the anchoring means have the form of a stud.

According to another particular feature in the embodiment, the head of the anchoring means have larger dimensions than the openings of the second plate, the anchoring means being fixed into a vertebra, the second plate is sandwiched in between the head of the anchoring means and said vertebra.

According to another particular feature in the embodiment, the upper plate is bulged on at least a part of its upper surface to adapt to the form of the vertebrae.

Another aim is to propose an insertion device, between two vertebrae, of intervertebral disc prostheses constituted by a lower plate, an upper plate and a mobile core at least relative to the lower plate. It would be advantageous for the prosthesis insertion device between two vertebrae to allow the prosthesis to be kept sterile, to position it facing the opening made by the surgeon between the two vertebrae, to have it enter this opening by translation then to withdraw the device leaving the prosthesis inserted in its opening.

This aim is attained by an insertion device, between two vertebrae, of intervertebral disc prostheses constituted by a first plate, an second plate and a mobile core at least relative to the second plate, characterised in that it comprises a clip whereof the front surface has a form provided to fit the form of the front edge of the prosthesis and whereof at least two edges are equipped with a gripping means.

According to another particular feature in the embodiment, the gripping means present on the clip may be exhibited, for example, as two flexible blades mounted on the lateral edges of the clip and holding the prosthesis by pinching the lateral edges of the upper and lower plates of the prosthesis.

According to another particular feature in the embodiment, the front surface of the clip has a form provided to fit the form of the front edge of the prosthesis, on one hand, owing to its height at least substantially equal to the height of the prosthesis, so as to come into contact with the front edges of each of the plates of the prosthesis and, on the other hand, to at least one groove in at least the median part of the front surface of the clip to likewise come in contact with the front edge of the core which is slightly set back relative to the front edges of the plates.

According to another particular feature in the embodiment, the rear surface of the clip can be pushed by a first end of a rod, known as a guide, equipped with a pusher at its other end and with a limit stop at a variable position along the guide for limiting the length of the sliding of the guide inside a body of a charger equipped with a head in which is arranged a space dimensioned for receiving the prosthesis and the clip, the position of the limit stop on the guide being adjustable such that the prosthesis, held by the clip, exits from the head of the charger and is centred relative to the vertical axis of the two vertebrae between which it must be implanted when the limit stop contacts the body of the charger.

According to another particular feature in the embodiment, the front end of the gripping means of the prosthesis present on at least two edges of the clip is larger than their back end at which the width of the clip is substantially equal to the width of the space in the head of the charger, such that, when the prosthesis and the clip are in the head of the charger, the prosthesis is held firmly by the gripping means of the clip which are then compressed between the prosthesis and the internal wall of the space arranged in the head of the charger and, when the prosthesis exits from the head of the charger, it is held less firmly by the clip, so as to be able to be released therefrom.

BRIEF DESCRIPTION OF FIGURES

Other particular features and advantages of the embodiments of present invention will emerge more clearly from the description hereinbelow, given in reference to the attached drawings, in which:

FIG. 7b illustrates it according to the section plan D-D of FIG. 7a.

DESCRIPTION OF PREFERRED EMBODIMENTS

Figure 1A:
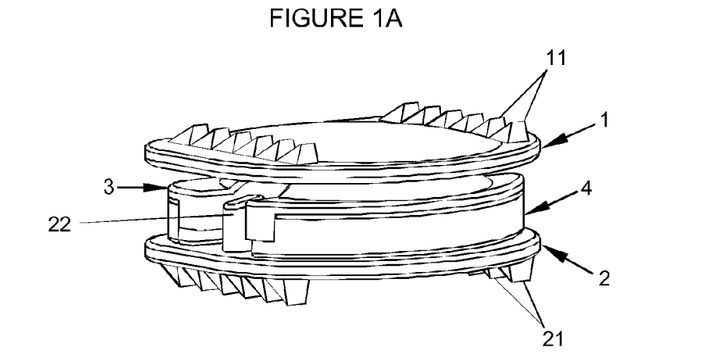
FIG. 1a illustrates a perspective view of a prosthesis according to an embodiment of the invention, viewed from the front.
Figure 1B:
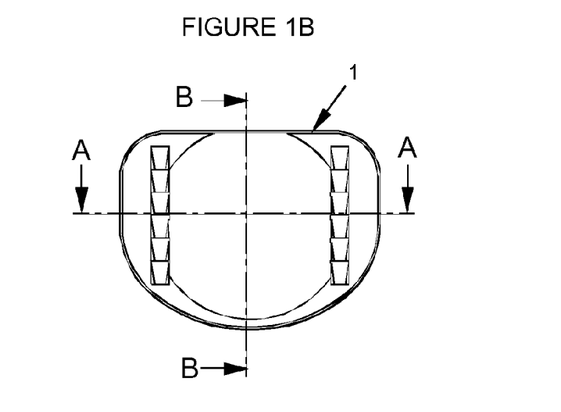
FIG. 1b illustrates a top view of a prosthesis with the planes of section A-A and B-B, respectively of FIGS. 1c and 1d.
Figure 1C:
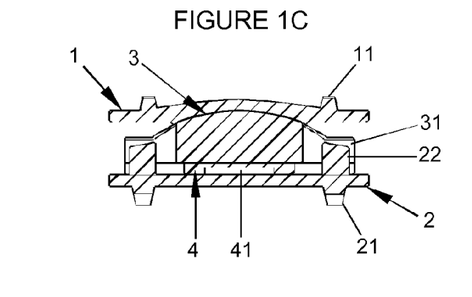
Figure 1D:
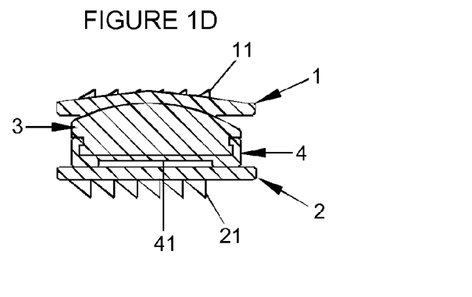

The intervertebral disc prosthesis according to an embodiment of the present invention is comprised of a first plate (1) articulated relative to a second plate (2) by means of a core (3), as evident in particular in FIGS. 1a, 1c and 1d. In the following description, the first plate (1) is called the upper plate and the second plate (2) is called the lower plate, according to the orientation given to the prosthesis shown in the drawings. Those of skill will recognize after appreciating this disclosure that the prosthesis could be inversely oriented between the vertebrae, so that the first plate (1) would be the lower plate and the second plate (2) would be the upper plate. An advantage of the prosthesis according to the present invention is that it comprises simple pieces which can be dimensioned so that the prosthesis is placed on the cervical spine.

The core (3) is of less thickness (for example 3 mm in a preferred embodiment) for a cervical prosthesis or thicker (for example 15 mm in a preferred embodiment) for a lumbar prosthesis.

Figure 4A:
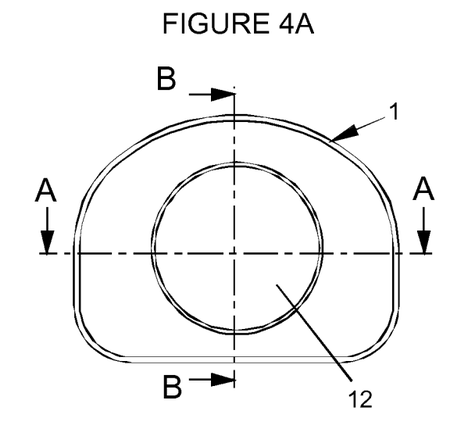
FIG. 4a illustrates a bottom view of the upper plate of the prosthesis, with the planes of sections A-A and B-B, respectively of FIGS. 4c and 4d.
Figure 4B:
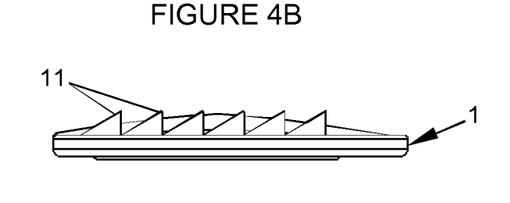
FIG. 4b illustrates a side view of the upper plate of the intervertebral disc prosthesis according to an embodiment of the invention.
Figure 4C:
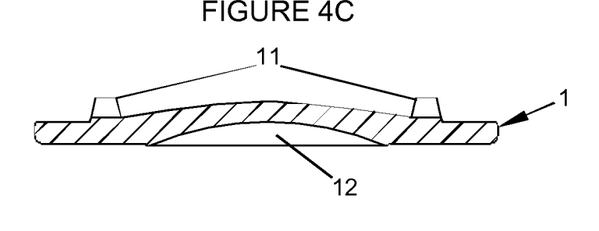
Figure 4D:
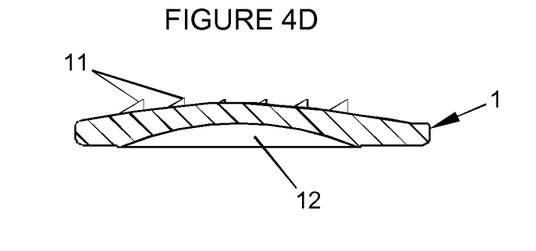
Figure 5A:
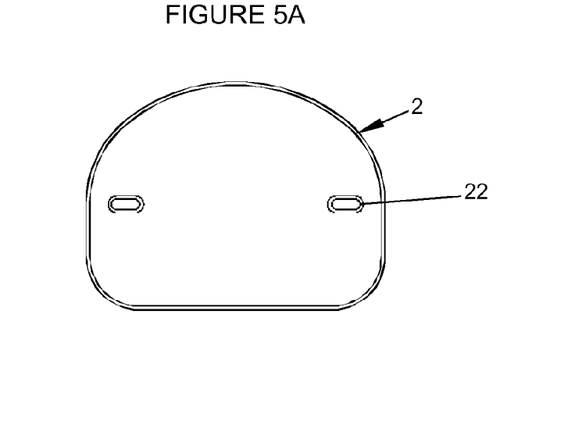
FIG. 5a illustrates a top view of the lower plate of the prosthesis.
Figure 5B:
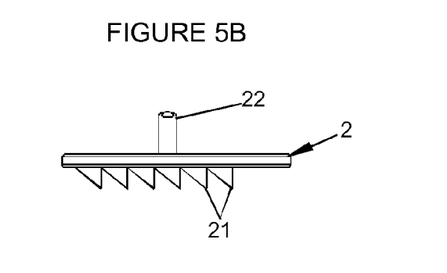
FIGS. 5b and 5c illustrate respectively side views and front views of the lower plate of the prosthesis and FIGS. 5d and 5e illustrate, in perspective, respectively, a top view and a bottom view of the lower plate of the intervertebral disc prosthesis according to an embodiment of the invention.
Figure 5C:
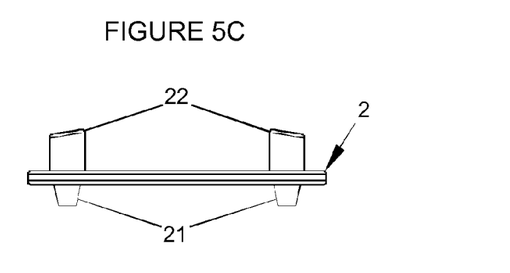
Figure 5D:
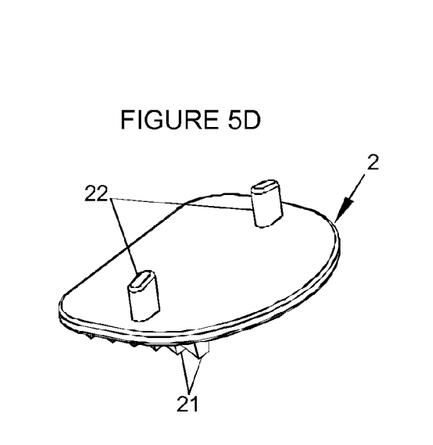
Figure 5E:
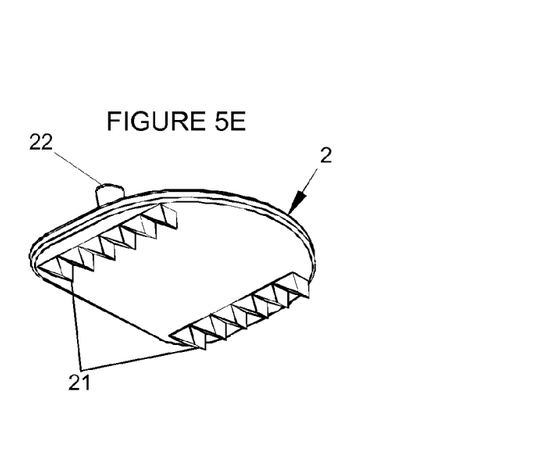

In another embodiment, a part of the upper surface of the upper plate (1) is bulged, as shown in FIGS. 4b to 4d, so as to better adapt to the vertebra on which the prosthesis is intended to be placed, the lower surface of the vertebrae being hollow. The bulged part of the upper plate (1) is then situated in the front part of the upper plate, as shown in particular in FIG. 4d. The lower plate (2) is substantially flat and in preferred embodiments, its lower surface has no requirement to be bulged or hollow, since the upper surface of the vertebrae is substantially flat.

In the embodiment of FIGS. 1a to 1d, 4b to 4d and 5b to 5e, the upper surface of the upper plate (1) and the lower surface of the lower plate (2) are provided with teeth or notches (11, 21) situated in the region of at least two edges of the prosthesis. These notches (11, 21), oriented so as to prevent sliding of the prosthesis, serve as anchors for the prosthesis at times when the osseous tissue adheres to these surfaces of the plates in contact with the vertebrae. In fact, the osseous tissue, in the few weeks following surgical intervention for implanting the prosthesis, will invade the surfaces with which it is in contact. A porous biocompatible coating is provided on these surfaces to allow adhesion of the osseous tissue and its definitive fusion with the prosthesis.

In another embodiment, the lower surface of the core (3) is enclosed by a protective shell (4) of the core. This protective shell (4) is, for example, drilled, in the centre of its lower surface, with at least one hole (41), for example a dummy, which improves sliding on the upper surface of the lower plate (2). In a simpler variant embodiment, in the absence of this protective shell (4), it is the lower surface of the core (3) which, for example, will be pierced by a dummy hole in its centre. The core alone will then have substantially the same appearance as the ensemble made up by the core (3) and its protective shell (4), such as in the embodiment described hereinafter and illustrated in FIGS. 2a to 2e. The size and form, for example oval, of the hole (41) through the core (3) or the protective shell (4) are adapted to the size and form of the core or of the protective shell. The hole will have been made so that the angles formed by its edges (411) are softened to reduce friction on the lower plate. This hole (41) of adapted dimensions can of course be replaced by a plurality of smaller holes, whereof the extent will be adapted to the size and form of the core or of the protective shell. For example, a multitude of concave minuscule alveoli could be arranged on the lower surface of the core or of the protective shell.

In a variant embodiment the dummy hole (41) present at least on the lower surface of the core (3) or of the protective shell (4) of the core is prolonged by grooves (410) which extend as far as the periphery of this lower surface. These grooves (410) thus form channels via which interstitial liquid from surrounding tissue can slide between the lower surface of the core (3) or of the protective shell (4) and play a lubricating role to improve sliding of the core (3) on the upper surface of the lower plate (2).

The hole (41) and the eventual grooves (410) may be such that the area of contact between the lower surface of the core (3) and the upper surface of the lower plate (2) is substantially equal to the area of contact between the upper surface of the core (3) and the lower surface of the upper plate (1). The constraints applied to the prosthesis will thus be absorbed equally by both surfaces of the core (3) in this embodiment, which will allow reducing frictions and improving the life duration of the core by optimizing the displacement of the core (3) relative to the plates (1, 2).

Figure 2A:
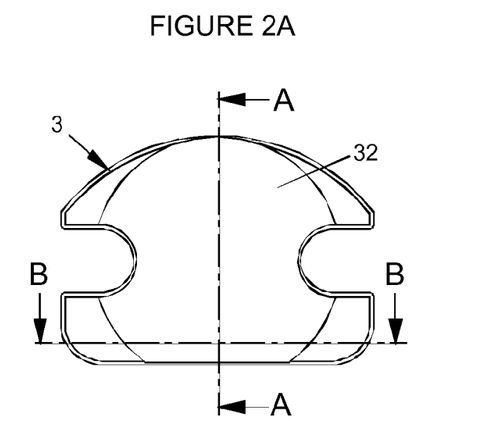
FIG. 2a illustrates a top view of the core equipped with its protective shell in an embodiment of the invention, with the planes of sections A-A and B-B, respectively of FIGS. 2b and 2c.
Figure 2B:
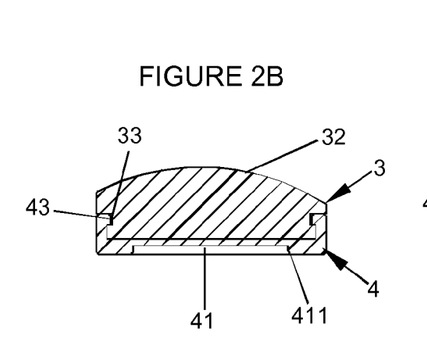
FIGS. 2d and 2e illustrate, in perspective, respectively, a top view and a bottom view of the core equipped with its protective shell.
Figure 2C:
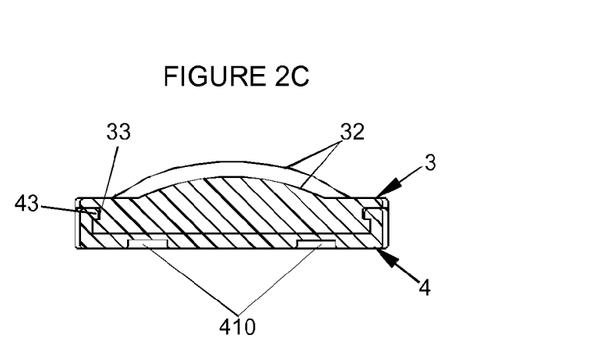
Figure 2D:
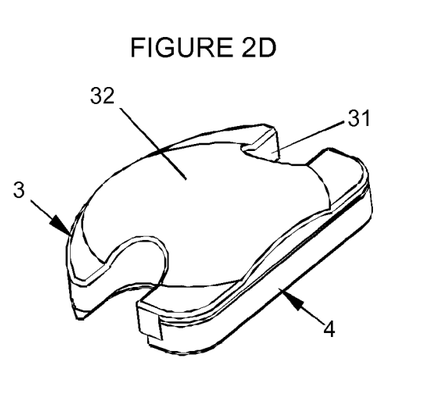
Figure 2E:
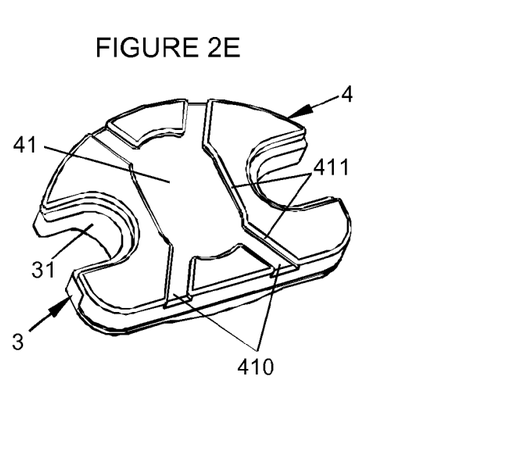
Figure 3A:
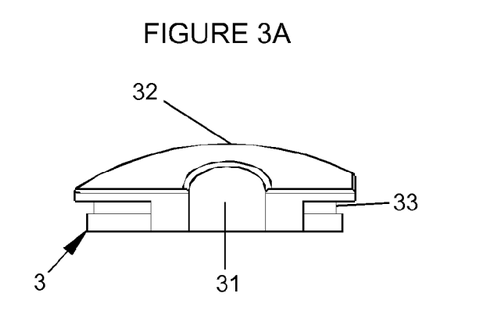
FIGS. 3a and 3b illustrate respectively a profile view and a top view in perspective of a core deprived of a protective shell in an embodiment of the invention.
Figure 3B:
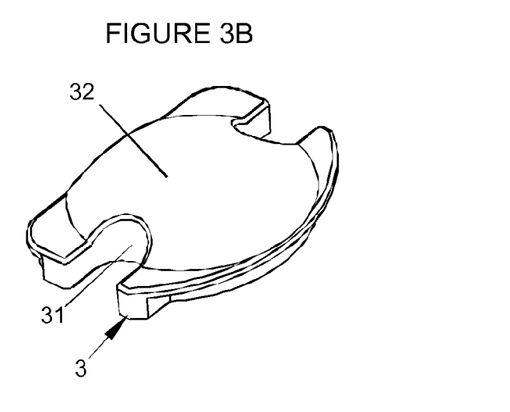
Figure 3C:
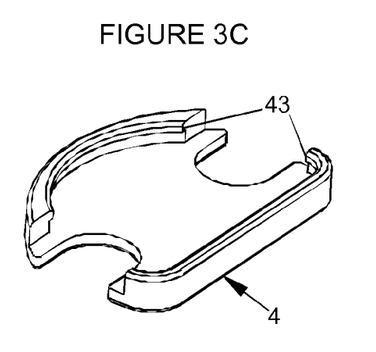
FIGS. 3c and 3d illustrate, in perspective, respectively, a top view and a bottom view of the protective shell of the core according to an embodiment of the invention.
Figure 3D:
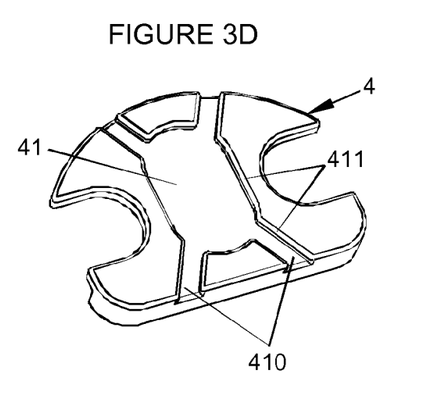

In the embodiment where the lower surface of the core (3) is enclosed by a protective shell (4), the lower part of the core may be narrower than its upper part, such that once the protective shell (4) is mounted on the lower part, the core has substantially homogeneous dimensions, as shown in FIGS. 2a to 2e. On the circumference of the core, substantially at the centre of its thickness, a groove (33), shown in FIGS. 2b, 2c and 3a, complementary to a groove (43), illustrated in FIGS. 2b, 2c and 3c, present on the internal part of the edges of the protective shell (4), provides cohesion of the ensemble made up by the core (3) and its protective shell (4). The core (3) will then be simply encased in the protective shell (4) when the prosthesis is mounted.

The core (3) in this embodiment has, on at least one part of its upper surface, a convex part (32), evident particularly in FIGS. 2a to 2d, 3a and 3b, complementary to a concave part (12) of the upper plate (1), evident particularly in FIGS. 4a, 4c and 4d. This concave part (12) permits inclination of the upper plate (1) when the patient wearing the prosthesis bends over. The lower surface of the core (3) or of the protective shell (4) and the upper surface of the lower plate (2) could be plane, or substantially flat, so as to permit clearance of the core (3) relative to the lower plate (2), both in translation according to an axis substantially parallel to the lower plate (2), and in rotation about an axis substantially perpendicular to the lower plate (2). During movements made by the patient wearing the prosthesis, this inclination of the upper plate (1) and this clearance of the core will allow displacement of the core (3) towards the ideal position to absorb the constraints applied to the prosthesis. The movement between the upper plate (1) and the core (3), as well as the clearance of the core (3) relative to the lower plate (2) thus allow the patient to move, and, optionally, to eliminate the defects of positioning the prosthesis. This clearance likewise has the advantage of preventing premature wear due to the constraints applied to the prosthesis. The dummy hole (41) bored in the lower surface of the core (3) or of the protective shell (4) will help improve sliding of the core on the upper surface of the lower plate, so that the core can find the ideal position for absorbing the constraints imposed on the prosthesis as fast and as easily as possible. For good absorption of the constraints, the core (3) could, for example, be made of polyethylene, or other materials that are compressible and may simulate physical properties of natural intervertebral discs such as elasticity, for example.

According to an embodiment of the invention, the lower surface of a core (3) made of compressible material could be enclosed by a metallic protective shell (4), permitting better sliding on the lower metallic plate (2) and reduction in creep of the compressible material. The sliding of the core will be improved by a hole (41), for example a dummy, bored in the lower surface of the protective shell (4).

In the embodiment of FIGS. 1a, 1c and 5a to 5e the lower plate (2) comprises two contact plates (22) situated opposite one another on two edges of the lower plate (2), at each lateral sides of the lower plate (2). Each contact plate (22) comprises male structure of the lower plate (2) and can penetrate female structure of the core, constituted in this embodiment by a recess (31) of the core (3) on two of its edges. In the embodiment shown in these figures, the dimensions of each recess (31) of the core (3) are slightly greater than those of each nib (22) of the lower plate (2) so as to limit clearance of the core (3) relative to the lower plate (2), both in translation along an axis substantially parallel to the lower plate (2), and in rotation about an axis substantially perpendicular to the lower plate (2).

In the embodiment where a core (3) made of compressible material is provided with a protective metallic shell (4) sliding on a lower metallic plate, the protective shell could be in an adapted form so that it is not in contact with a metallic limit stop of the lower plate. Such a result can be obtained, for example, thanks to the fact that the edges of the protective shell (4) are slightly offset from the limit stops of the core. This variant embodiment can prove necessary since, in a living organism, it is preferable to avoid the shocks between two metallic materials, which risk projecting metallic particles into the surrounding tissue and causing complications.

In a variant embodiment not shown, the dimensions of each recess (31) of the core (3) are substantially the same as those of each nib (22) of the lower plate (2), so as to avoid any clearance of the core (3) relative to the lower plate (2), both in translation and in rotation. In the latter case, the only permitted movement of the prosthesis is that of the upper plate (1) relative to the core (3).

In a variant embodiment not shown, the contact plates (22) are replaced by nibs curved towards the interior of the prosthesis, above the edges of the core (3), so as to prevent the core from being raised. In another variant, one of the nibs is replaced by a contact plate (or pin) equipped with a hole in which, for example, a dowel fixes a plate (or hasp). The ensemble made up by the hasp fixed on the contact plate will have the same form as the nib of the opposite side and will fulfil the same function with the added advantage of facilitating mounting of the different pieces of the prosthesis. In a variant embodiment, the two nibs are each replaced by a contact plate to which a hasp is fixed.

In another variant embodiment not shown, the contact plates (22) of the lower plate (2) are replaced by half dog points. The core (3), by way of complement, does not comprise recesses (31), but two wells under its lower surface. The dimensions of the half dog points of the lower plate (2) and of the wells of the core (3) will be adapted according to the desired result, by choice, of slight clearance of the core in translation and in rotation or any clearance.

In another embodiment not shown, the contact plates (22) of the lower plate (2) are replaced by walls, positioned opposite one another, in the vicinity of two substantially parallel edges of the lower plate, but more towards the interior of the prosthesis than the contact plates (22). The core (3) comprises recesses complementary to the walls. The dimensions of each recess of the core of this embodiment are, either slightly greater, or substantially the same as those of each wall of the lower plate, so as to allow or not slight clearance in translation and in rotation.

In yet another embodiment not shown, the female cooperation means are situated on the lower plate (2) and the male cooperation means on the core (3).

An intervertebral disc prosthesis according to many embodiments of the present invention help to correct the defects of lordosis. The presence of an acute angle, for example of between 0° and 15°, in the postero-anterior direction, between the upper plate (1) and the lower plate (2) of the prosthesis could be desired. To adjust the angle necessary as a function of the patient, it suffices to select a core (3) with an appropriate angle between the average plane representing its upper surface and the plane passing through its lower surface. Such an angle could likewise be obtained by making an upper plate, including the plane means representing its lower and upper surfaces forming an angle. Another possibility involves the lower plate whereof the plane means representing its lower and upper surfaces form an angle. Another possibility consists of a position of the core slightly offset to the rear or the front relative to the centre of the prosthesis including the plates which will then form an angle. This slightly offset position of the core can, for example, be maintained due to adjustable positioning of the male and female limit stops.

In the event where the male structure or stop in the vicinity of the edges of the core (i.e., near the periphery of the core) and the female structure or stops are situated in the vicinity of the edges of the lower plate (i.e., near the periphery of the lower plate), a lordosis core (by the fact that if forms an acute angle in the postero-anterior direction) can then be made solid with the plate by a projection penetrating a cavity or opening in the lower plate. If the surgeon wants lordosis determined for a patient, he will select a core (3) which cannot have any clearance relative to the lower plate (2). However, if he only wants the lordosis to remain within a range of values, he will select a core which can have slight clearance in translation and in rotation relative to the lower plate (2), but about a position imposing slight permanent inclination of at least one of the plates.

The intervertebral disc prosthesis according to a variety of embodiments of the present invention can, in variant embodiments, be anchored solidly, from when implanted, in the vertebral column to prevent the prosthesis from migrating under the effect of the resulting transversal of the force exerted by the vertebral column on the prosthesis in place, an important consideration in lordosis. In this case, the lower plate (2) comprises one or more openings situated in the vicinity of the rear side of the prosthesis, receiving anchors of a variety of types.

Therefore, in a variant embodiment, the openings in the lower plate (2) are circular and the anchors preferably have the shape of studs, with a head having a size greater than that of the openings to allow the lower plate (2) to be sandwiched between the head of the anchors and the vertebra on which the prosthesis is anchored. For greater security, the openings could be made such that the anchors and the lower plate form an angle of less than or equal to 90°.

Figure 6A:
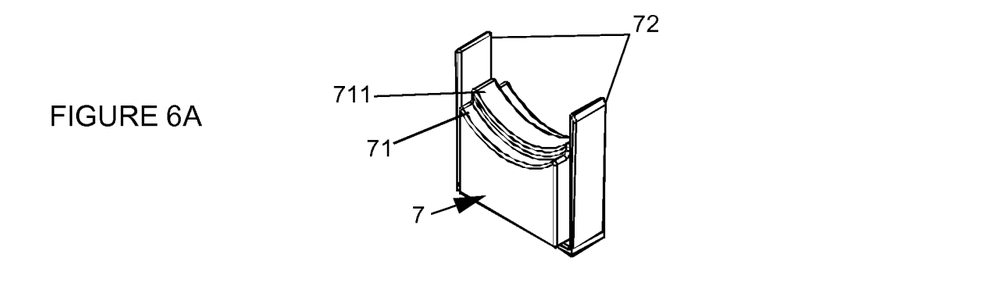
FIG. 6a illustrates a view in perspective of the clip of the insertion device of intervertebral disc prostheses between two vertebrae.
Figure 6B:
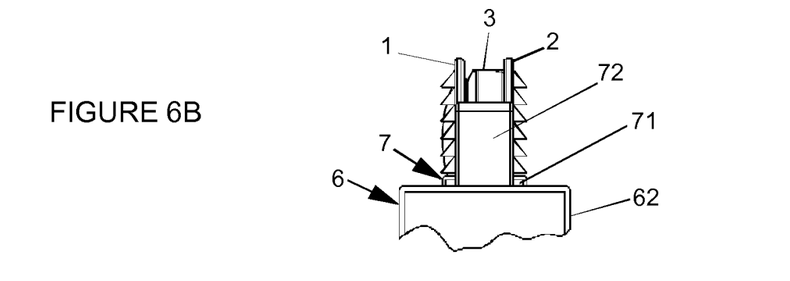
FIGS. 6b and 6c illustrate a partial profile and top view, respectively, of the head of the charger of the prosthesis insertion device between two vertebrae, with the prosthesis held by the clip in extended position.
Figure 6C:
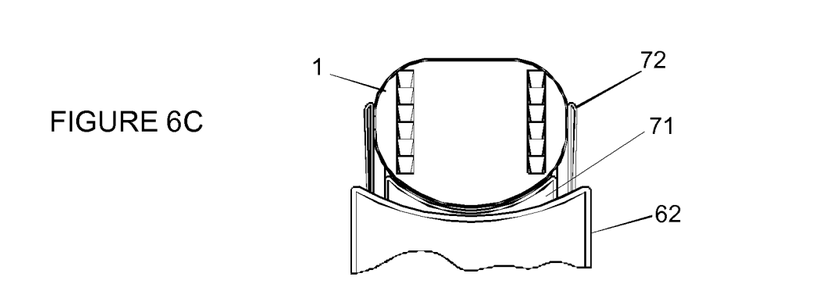
Figure 6D:
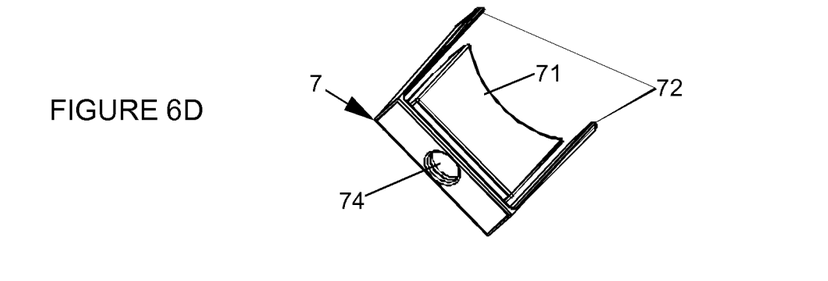
FIG. 6d illustrates a view in perspective of the clip of the insertion device of intervertebral disc prostheses between two vertebrae.
Figure 7A:
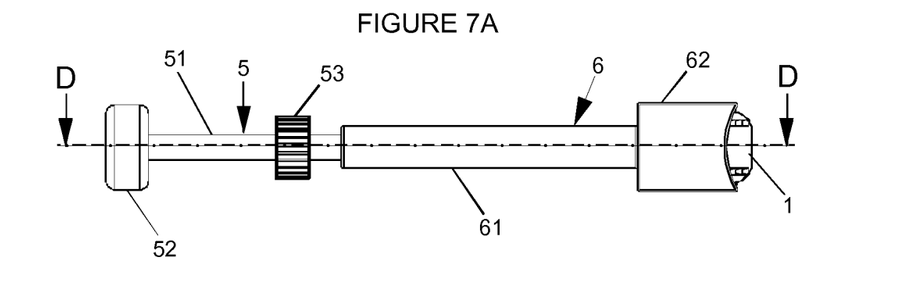
FIG. 7a illustrates a top view of the complete prosthesis insertion device between two vertebrae when the prosthesis held by the clip is retracted into the head of a charger.
Figure 7B:
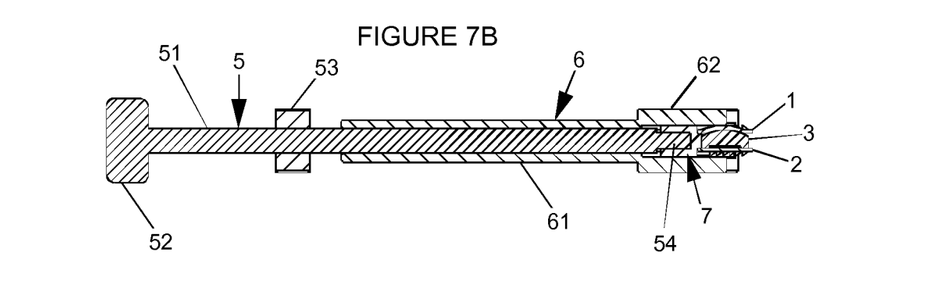
Figure 7C:
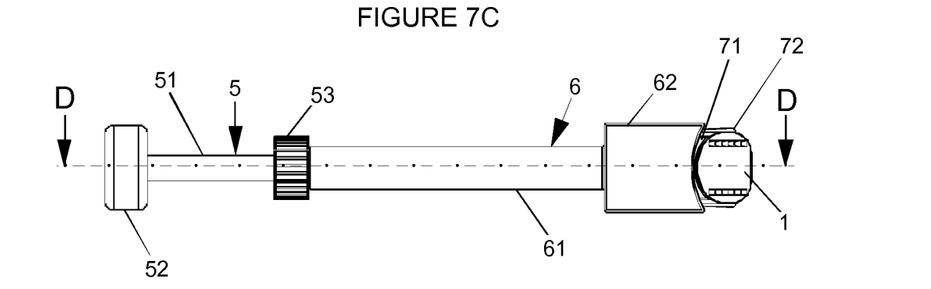
FIG. 7c illustrates a top view of the complete prosthesis insertion device between two vertebrae when the prosthesis held by the clip is extended from the head of the charger.
Figure 7D:
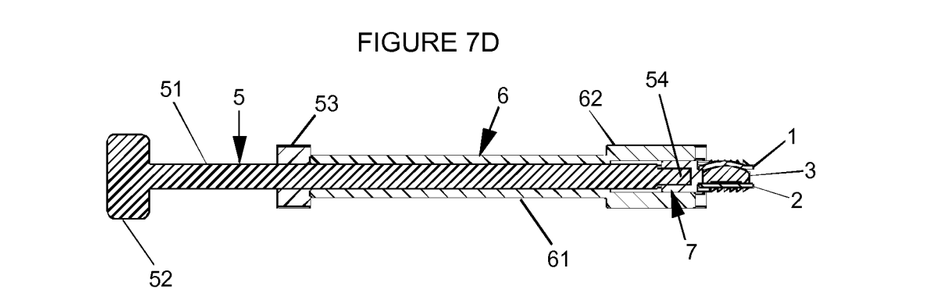
FIG. 7d illustrates it according to the section plan D-D of FIG. 7c.

Intervertebral disc prostheses are typically not easy to implant in the patient. This difficulty is exacerbated by the fact of the relative mobility of the pieces of the prostheses. It is thus preferred to associate these prostheses with a device allowing it to be held and inserted between the vertebrae. Such a device according to an embodiment of the present invention is made up of a clip (7) whereof the front surface (71) has a shape provided to fit the form of the front edge of the prosthesis. This clip (7) has a fitting on its front that grips (72) the prosthesis. These gripping means (72) can, for example, be two (72) flexible blades mounted on the lateral edges of the clip and can hold the prosthesis by pinching the lateral edges of the upper and lower plates of the prosthesis. The front surface (71) of the clip (7) has preferably, for example, a height at least substantially equal to the height of the prosthesis, so as to come into contact with the front edges of each of the plates of the prosthesis.

In an embodiment of the invention, a groove (711) is present in the median part of the front surface (71) of the clip (7) so as to come into contact with the front edge of the core, slightly set back relative to the front edges of the plates. There can of course be several grooves fitting the shape of the prosthesis. The front surface (71) of the clip (7) provided with the groove (711) thus fits the form of the front edge of the prosthesis when in contact with the three elements making up the prosthesis. The clip thus helps hold the prosthesis and push it homogeneously towards its opening between two vertebrae. This clip (7) is provided to hold the prosthesis and to be inserted into a charger (6) (or loader). This charger (6) has a head (62) in which a space is arranged to receive the clip holding the prosthesis and a body (61) provided to slide about a rod, called a guide (5). The rear surface of the clip (7) can be provided with a hole in its centre, provided to insert an end (54) of the guide (5) so that the guide (5) can hold and push the clip (7). The guide (5) is equipped with a pusher (52) at its other end, which will help push the clip and the prosthesis out of the head (62) of the charger (6) by having the guide (5) slide in the body (61) of the charger (6). An adjustable stop is mounted on the guide (5). For example, a threaded ring (53) is screwed around the guide. This ring serves as a stop (53) to the guide when it slides in the body (61) of the charger (6). The position of the stop (53) will be adjusted, as a function of the size of the vertebra, so that when the stop (53) of the guide (5) comes into contact with the body (61) of the charger (6), the end (54) of the guide (5) will have pushed the clip (7) as far as a position where the prosthesis, held by the flexible blades (72) of the clip, is now out of the head (62) of the charger (6) and centred relative to the axis of the vertebral column.

In an embodiment of the prosthesis according to the invention, as described earlier, the upper (1) and lower (2) plates are provided with anchors as such teeth or notches (11 and 21) for example, on their surface in contact with the vertebrae. These anchors or notches (11, 21) are oriented so as to oppose displacement of the prosthesis in the direction of withdrawal of the clip (7), once the prosthesis is entered in its opening between two vertebrae, made in advance by the surgeon. These notches (11, 21) are thus oriented so as to allow the prosthesis to return to its opening but not come out when the surgeon pulls back the clip (7) holding the prosthesis. On the other hand, the front end of the gripping means (72) of the prosthesis is larger (thicker) than their back end. The width of the clip at its back end is substantially equal to (or slightly smaller than) the width of the space in the head (62) of the charger (6). Thanks to these substantially equal dimensions of the space inside the head (62) of the charger (6) and of the prosthesis and the clip (7), when both the latter are in the head (62) of the charger (6), the prosthesis is solidly held by the flexible blades (72) of the clip (7) whereof the front ends are compressed between the prosthesis and the internal wall of the space made in the head (62) of the charger (6). When the surgeon presses on or strikes the pusher (52) of the guide, the prosthesis exits from the head (62) of the charger and it is held less firmly by the clip (7) since the back ends of the flexible blades (72) are less compressed than were the front ends. The prosthesis could then be released from the clip by pulling back the insertion device, owing to the presence of the notches on the lower and upper plates, allowing the prosthesis to remain in its opening between the two vertebrae.

The present invention allows embodiments in numerous other specific forms without departing from the spirit of the invention. As a consequence, the present embodiments must be considered by way of illustration only, and can be modified within the scope defined by the range of the attached claims, and thus, the invention should be.

Although the present invention has been described in detail, it will be apparent to those skilled in the art that many embodiments taking a variety of specific forms and reflecting changes, substitutions and alterations can be made without departing from the spirit and scope of the invention. Therefore, the described embodiments illustrate but do not restrict the scope of the claims.

The invention claimed is:

1. A system for treatment of a spine comprising:
   an intervertebral disc prosthesis for insertion between adjacent vertebrae comprising
      a first plate having a curved articulation surface and a vertebral contact surface,
      a second plate having a substantially flat articulation surface and a vertebral contact surface,
      a core having a curved surface in contact with at least a part of the curved articulation surface of the first plate and a substantially flat surface in contact with at least a part of the substantially flat articulation surface of the second plate, the core displaceable in translation along an axis substantially parallel to the substantially flat articulation surface of the second plate and in rotation about an axis substantially perpendicular to the substantially flat articulation surface of the second plate, and
      a plurality of limit stops each configured to limit translation and rotation of the core, each limit stop comprising a contact plate disposed proximal to a lateral edge of the second plate and a cooperating recess disposed along a lateral edge of the core;

a clip configured to hold the prosthesis during insertion of the prosthesis between adjacent vertebrae comprising a first lateral clip edge and a second lateral clip edge, a front surface having a form complementary to a form of a front edge of the prosthesis, with the clip having a loaded configuration in which the prosthesis is disposed between the first lateral clip edge and the second lateral clip edge with one lateral edge of the second plate in contact with the first lateral clip edge, an opposite lateral edge of the second plate in contact with the second lateral clip edge, and the front edge of the prosthesis in contact with the front surface of the clip; and an insertion instrument body comprising
a head sized to accept the clip in the loaded configuration,
a rod attachable to the clip and movable between a first position in which the clip is retracted at least partially in the head and a second position in which the clip is extended at least partially from the head,
a rod stop configured to limit movement of the rod and,
an internal wall of the head sized to compress the first lateral clip edge and the second lateral clip edge against the prosthesis with the clip retracted at least partially in the head.

2. The system according to claim 1 in which the prosthesis has an insertion direction, and comprises vertebral anchors having teeth oriented to oppose displacement of the prosthesis in a direction opposite the insertion direction.

3. The system according to claim 1 in which a biocompatible coating is disposed on the vertebral contact surfaces of the first and second plates.

4. The system according to claim 1 in which the vertebral contact surface of the first plate is at least partially bulged, and the vertebral contact surface of the second plate is substantially flat.

5. The system according to claim 1 in which the core has a channel formed in the substantially flat surface of the core.

6. The system according to claim 5 in which the channel is a groove.

7. The system according to claim 1 in which each of the first lateral clip edge and the second lateral clip edge comprises a flexible blade.

8. The system according to claim 7 in which the front surface of the clip has a first height, the front edge of the prosthesis has a second height, and the first height and the second height are substantially equal.

9. The system according to claim 8 in which the front surface of the clip has a first longitudinal face, a second longitudinal face, and a median longitudinal face, and, with the clip in the loaded configuration, the first longitudinal face contacts a front edge of the first plate, the second longitudinal face contacts a front edge of the second plate, and the median longitudinal face contacts a front edge of the core.

10. A system for treatment of a spine comprising:
an intervertebral disc prosthesis for insertion between adjacent vertebrae comprising
a first plate having a curved articulation surface and a vertebral contact surface,
a second plate having a substantially flat articulation surface and a vertebral contact surface,
a core having a curved surface in contact with at least a part of the curved articulation surface of the first plate and a substantially flat surface in contact with at least a part of the substantially flat articulation surface of the second plate, the core displaceable in translation along an axis substantially parallel to the substantially flat articulation surface of the second plate and in rotation about an axis substantially perpendicular to the substantially flat articulation surface of the second plate, and
a limit stop configured to limit translation and rotation of the core comprising a contact plate disposed proximal to a lateral edge of the second plate and a cooperating recess disposed along a lateral edge of the core;

a clip configured to hold the prosthesis during insertion of the prosthesis between adjacent vertebrae comprising a first lateral clip edge and a second lateral clip edge, with the clip having a loaded configuration in which the prosthesis is disposed between the first lateral clip edge and the second lateral clip edge with one lateral edge of the second plate in contact with the first lateral clip edge and an opposite lateral edge of the second plate in contact with the second lateral clip edge; and an insertion instrument body comprising a head sized configured to accept the clip in the loaded configuration.

11. The system according to claim 10 in which the vertebral contact surface of the first plate is at least partially bulged, and the vertebral contact surface of the second plate is substantially flat.

12. The system according to claim 10 in which the core has a channel formed in the substantially flat surface of the core.

13. The system according to claim 12 in which the channel is a groove.

14. The system according to claim 10 in which each of the first lateral clip edge and the second lateral clip edge comprises a flexible blade.

15. The system according to claim 10 in which the clip comprises a front surface having a form complementary to a form of a front edge of the prosthesis, the front surface of the clip has a first height, the front edge of the prosthesis has a second height, and the first height and the second height are substantially equal.

16. The system according to claim 15 in which the front surface of the clip has a first longitudinal face, a second longitudinal face, and a median longitudinal face, and, with the clip in the loaded configuration, the first longitudinal face contacts a front edge of the first plate, the second longitudinal face contacts a front edge of the second plate, and the median longitudinal face contacts a front edge of the core.

17. A system for treatment of a spine comprising:
an intervertebral disc prosthesis for insertion between adjacent vertebrae comprising
a first plate having a curved articulation surface and a vertebral contact surface,
a second plate having a substantially flat articulation surface and a vertebral contact surface,
a core having a curved surface in contact with at least a part of the curved articulation surface of the first plate and a substantially flat surface in contact with at least a part of the substantially flat articulation surface of the second plate, the core displaceable in translation along an axis substantially parallel to the substantially flat articulation surface of the second plate and in rotation about an axis substantially perpendicular to the substantially flat articulation surface of the second plate, and a pair of limit stops, each disposed on an opposite side of the prosthesis and each comprising a vertically oriented contact plate disposed proximal to an edge of the second plate and having first and second generally parallel planar stop surfaces, and a recess disposed on an edge of the core and configured to cooperate with the vertically oriented contact plate, having first and second generally parallel planar stop surfaces configured to engage, respectively, the first and second generally parallel planar stop surfaces of the contact plate to limit translation of the core along the substantially flat articulation surface of the second plate, with the first generally parallel planar stop surface of the recess contacting the first generally parallel planar stop surface of the vertically oriented contact plate at a first limit of translation of the core and the second generally parallel planar stop surface of the recess contacting the second generally parallel planar stop surface of the vertically oriented contact plate at a second limit of translation of the core, with the first and second limits of translation defining a nonzero range of translation and rotation of the core with respect to the second plate a clip configured to hold the prosthesis during insertion of the prosthesis between adjacent vertebrae comprising a first lateral clip edge and a second lateral clip edge, with the clip having a loaded configuration in which the prosthesis is disposed between the first lateral clip edge and the second lateral clip edge with one lateral edge of the second plate in contact with the first lateral clip edge and an opposite lateral edge of the second plate in contact with the second lateral clip edge; and an insertion instrument body comprising a head sized configured to accept the clip in the loaded configuration.

18. The system according to claim 17 in which each of the first lateral clip edge and the second lateral clip edge comprises a flexible blade.

19. The system according to claim 17 in which the clip comprises a front surface having a form complementary to a form of a front edge of the prosthesis, the front surface of the clip has a first height, the front edge of the prosthesis has a second height, and the first height and the second height are substantially equal.

20. The system according to claim 19 in which the front surface of the clip has a first longitudinal face, a second longitudinal face, and a median longitudinal face, and, with the clip in the loaded configuration, the first longitudinal face contacts a front edge of the first plate, the second longitudinal face contacts a front edge of the second plate, and the median longitudinal face contacts a front edge of the core.

* * * * *